United States Patent [19]

Cotrel et al.

[11] Patent Number: 4,753,933
[45] Date of Patent: * Jun. 28, 1988

[54] ANXIOLYTIC AMIDES DERIVED FROM CERTAIN 1,8-NAPHTHYRIDINE-2-AMINES

[75] Inventors: Claude Cotrel, Paris; Claude Guyon, Saint-Maur-Des-Fosses; Gerard Roussel, Soisy-Sur-Seine; Gerard Taurand, Creteil, all of France

[73] Assignee: Rhone-Poulenc Sante, Courbevoie, France

[*] Notice: The portion of the term of this patent subsequent to Feb. 10, 2004 has been disclaimed.

[21] Appl. No.: 2,929

[22] Filed: Jan. 13, 1987

[30] Foreign Application Priority Data

Jan. 16, 1986 [FR] France .................... 86 00556

[51] Int. Cl.⁴ .............. A61K 31/435; C07D 471/04
[52] U.S. Cl. .......................... 514/228.2; 514/253; 514/300; 514/234.5; 544/58.6; 544/127; 544/238; 544/362; 546/122
[58] Field of Search .......... 546/122; 544/58.6, 127, 544/238, 362; 514/222, 228, 232, 234, 253, 300

[56] References Cited

U.S. PATENT DOCUMENTS 4,642,308 2/1987 Cotrel et al. .................... 546/122

FOREIGN PATENT DOCUMENTS 1006725 4/1952 France .

*Primary Examiner*—Richard A. Schwartz
*Assistant Examiner*—Bernard L. Dentz

*Attorney, Agent, or Firm*—Stevens, Davis, Miller & Mosher

[57] ABSTRACT

The invention provides new substituted amides of formula:

R—CONH—Het in which: either R is cycloalkyl (3 to 6 carbons), cyclohexadienyl, phenyl, substituted phenyl or a heterocyclic systems chosen from 3-pyridyl, alkyloxy-3-pyridyl, thienyl, alkylthienyl, furyl, tetrahydropyridyl, pyridazinyl, and alkylpyridazinyl, and Het is 1,8-naphthyridin-2-yl substituted at the 7-position by alkyloxy, alkylthio or alkylsulphinyl, themselves substituted with alkylamino or dialkylamino (in which the alkyl portions can form, with the nitrogen atom, a 5- or 6-membered heterocyclic system optionally containing another heteroatom chosen from O, S or N, and optionally substituted by alkyl) or by dialkylcarbamoyl or N-alkyl-N-(alkyloxycarbonyl)amino, or substituted at the 7-position by dialkylaminovinyl; or R is 4-(alkylamino)phenyl or 4-(alkyloxycarbonylamino)phenyl and Het is 1,8-naphthyridin-2-yl substituted at the 7-position by alkyloxy or alkylthio, the said alkyl radicals and alkyl portions containing 1 to 4 carbons, their salts, their preparations and pharmaceutical compositions which contain them.

These new substituted amides are especially active as anxiolytics, hypnotics, anticonvulsants, antiepileptics and muscle relaxants.

10 Claims, No Drawings

ANXIOLYTIC AMIDES DERIVED FROM CERTAIN 1,8-NAPHTHYRIDINE-2-AMINES

This invention relates to amides having pharmaceutical utility, to their preparation, and to compositions containing them.

In PCT Patent Application No. 84/00,489, benzamide derivatives of the formula:

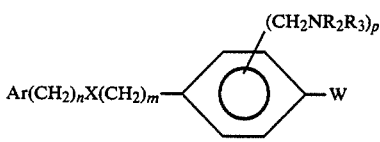

which are useful as antiarrhythmics are described.

In Dutch Patent Application No. 73/05,482 and U.S. Pat. No. 3,993,656, 1,8-naphthyridine derivatives of formula:

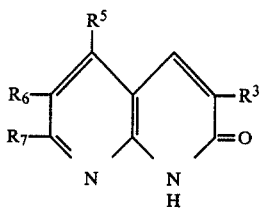

which are useful as bronchodilators and peripheral vasodilators or as hypotensive agents, are described.

The present invention provides new substituted amides of the formula:

and their acid addition salts in which either (A)R denotes cycloalkyl of 3 to 6 carbon atoms, cyclohexadienyl, phenyl, or phenyl substituted by 1 or 2 fluorine atoms, by hydroxyl, by alkyl or alkyloxy at the 3- or 4-position, by methylenedioxy at the 3- and 4-positions, by dialkylamino at the 2- or 3-position or by alkylamino or alkyloxycarbonylamino radical at the 4-position, or alternatively R denotes 3-pyridyl, alkyloxy-3-pyridyl, thienyl, alkylthienyl, furyl, tetrahydropyridyl, pyridazinyl or alkylpyridazinyl, and Het denotes 1,8-naphthyridin-2-yl substituted at the 7-position by alkyloxy, alkylthio or alkylsulphinyl said radicals being substituted by alkylamino, by dialkylamino (in which the alkyls can optionally form, with the nitrogen atom to which they are attached, a 5- or 6-membered heterocyclic system optionally containing another hetero atom chosen from nitrogen, oxygen and sulphur and optionally substituted by alkyl), by N-alkyl-N-(alkyloxycarbonyl)amino or by dialkylcarbamoyl, or the said 1,8-naphthyridinyl radical is substituted at the 7-position by dialkylamiovinyl, or (B)R denotes a 4-(alkylamino)phenyl or 4-(alkyloxycarbonylamino)phenyl, and Het denotes 1,8-naphthyridin-2-yl substituted at the 7-position by alkyloxy or alkylthio, the aforesaid alkyl radicals and alkyl portions being linear or branched and containing 1 to 4 carbon atoms each.

According to a feature of the invention, the amides of formula (I) in which R and Het are as defined above, with the exception of those where Het denotes a 7-dialkylaminovinyl-1,8-naphthyridin-2-yl radical, are prepared by reacting an acid of formula:

in which R is defined as above, or a reactive derivative of this acid, with an amine of formula:

in which Het is defined as above.

When the acid of formula (II) is employed, the reaction is preferably performed in the presence of a peptide-condensing agent such as a carbodiimide (e.g. dicyclohexylcarbodiimide) or N,N'-carbonyldiimidazole or 2-ethoxy-1-ethoxycarbonyl-1,2-dihydroquinoline, in an organic solvent such as an ether (e.g. tetrahydrofuran, dioxane, glyme, diglyme), an amide (e.g. dimethylformamide), a nitrile (e.g. acetonitrile) or a chlorinated solvent (e.g. methylene chloride, dichloroethane or chloroform), at a temperature between 0° C. and the refluxing temperature of the reaction mixture. The reaction is preferably performed at about 20° C.

When a reactive derivative of the acid of formula (II) is employed, it is possible to react the anhydride, a mixed anhydride, an acid halide or an ester [which can be chosen from the activated or unactivated esters of the acid of general formula (II)]. The reaction is then either performed in an organic medium, optionally in the presence of an acid acceptor such as a nitrogenous organic base (e.g. a trialkylamine, a pyridine, 1,8-diazabicyclo[5.4.0]undec-7-ene or 1,5-diazabicyclo[4.3.0]non-5-ene), in a solvent such as is mentioned above, or a mixture of these solvents, at a temperature of between 0° C. and the refluxing temperature of the reaction mixture, or performed in a two-phase aqueous organic medium in the presence of an alkali metal base or alkaline earth metal base (e.g. sodium hydroxide or potassium hydroxide) or an alkali metal carbonate or bicarbonate or alkaline earth metal carbonate or bicarbonate, at a temperature of between 0° and 40° C. It is also possible to work without a solvent at the melting point of the reaction mixture.

It is to be understood that, when the acid of formula (II) contains a hydroxy radical, the latter is protected beforehand, by any known method which does not adversely affect the remainder of the molecule. By way of example, it may be protected, in particular, by an acetyl radical which can be removed by treatment in basic medium, e.g. by treatment with ethanolic potassium hydroxide.

It is also to be understood that, when the acid of general formula (II) (or its reactive derivative) or the amine of general formula (III) bear a substituent containing a secondary amine, the latter is protected beforehand by any known method for protecting amines without affecting the remainder of the molecule.

For this purpose, any readily removable protective group may be used, chosen, in particular, from the groups customarily used in peptide chemistry, e.g. trifluoroacetyl, t-butoxycarbonyl, 2,2,2-trichloroethoxycarbonyl, trityl, benzyl, benzyloxycarbonyl, p-nitrobenzyloxycarbonyl, p-methoxybenzyloxycarbonyl or formyl groups.

When several protective radicals are present on the molecule, the removal can be performed simultaneously or successively.

By way of example:

when the protective radical is a t-butoxycarbonyl, trityl, p-methoxybenzyloxycarbonyl or formyl radical, the removal is performed in acid medium. Preferably, trifluoroacetic acid is used at a temperature between 0° and 30° C., or alternatively anhydrous or aqueous formic acid or paratoluenesulphonic or methanesulphonic acid is used in acetonitrile, at a temperature of between 20° C. and the refluxing temperature of the reaction mixture;

when the protective radical is a trifluoroacetyl radical, the removal is performed by treatment in basic medium. For example, it is performed in the presence of an alkali metal carbonate in aqueous alcoholic medium;

when the protective radical is a 2,2,2-trichloroethoxycarbonyl or p-nitrobenzyloxycarbonyl radical, the removal is performed by reduction (for example by treatment with zinc in acetic acid);

when the protective radical is a benzyl or benzyloxycarbonyl radical, the removal is performed by catalytic hydrogenation.

According to a further feature of the invention, the amides of formula (I) in which R is defined as above and Het denotes a substituted 7-alkylsulphinyl-1,8-naphthyridin-2-yl radical as defined in the general formula (I) can also be prepared by oxidation of the corresponding amide of general formula (I) in which R is as defined above and Het denotes a substituted 7-alkylthio-1,8-naphthyridin-2-yl radical as defined above.

The reaction is generally performed in the presence of an oxidizing agent, by any method customarily used for preparing a sulphoxide from a sulphide without affecting the remainder of the molecule. Among the known oxidizing agents, it is advantageous to use hydrogen peroxide, or an inorganic or organic peracid, e.g. periodic acid or 3-chloroperbenzoic acid.

It is advantageous to work in a chlorinated solvent (e.g. methylene chloride or chloroform) at a temperature of between 0° and 40° C.

It is to be understood that, in the alternative where the product of general formula (I) in which Het is a 7-alkylthio-1,8-naphthyridin-2-yl radical contains hydroxy or secondary amine groups, this product can be used in the protected state at the end of its preparation. The liberation of the protective radicals is then performed after the oxidation reaction, by any method which does not adversely affect the remainder of the molecule.

According to a further feature of the invention, the amides of formula (I) in which R is defined as above and Het is a 7-dialkylaminovinyl-1,8-naphthyridin-2-yl radical can be prepared by the action of a compound of formula:

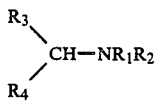

in which $R_1$ and $R_2$ denote alkyl radicals and $R_3$ and $R_4$, which are identical or different, denote either an alkyloxy group or a dialkylamino group, on a compound of formula:

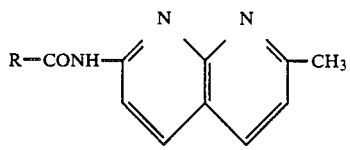

in which R has the corresponding definition.

The reaction is generally performed in an organic solvent such as an amide (e.g. dimethylformamide, dimethylacetamide or hexamethylphosphorotriamide) or a nitrile (e.g. acetonitrile), or in a mixture of these solvents, at a temperature of between 20° and 150° C.

When a reagent of general formula (IV) is used in which $R_3$ and/or $R_4$ denote a dialkylamino radical, this radical is chosen in such a way that the amine to which it corresponds is more volatile than $HNR_1R_2$.

The acids of general formula (II) can be prepared by application of the methods described below in the examples or by application of the following methods (or by methods analogous to these methods):

H. D. HARTOUGH, The Chemistry of heterocyclic compounds, thiophen and its derivatives, Interscience Publishers Inc. New York, page 363 (1952);

J. W. MASON, The Chemistry of heterocyclic compounds, Pyridazine carboxylic acids, John Wiley and Sons Inc., New York, page 407 (1973);

E. P. OLIVETO, The Chemistry of heterocyclic compounds Pyridinecarboxylic acids, Interscience Publishers Inc., page 179 (1962);

A. A. PETROV et al., Zhur Obshchei Khim, 26, 1588 (1956), M. E. KUEHNE et al., Org. Synth., 43, 22 (1968), S. HUNIG et al., Chem. Ber., 90, 238 (1957) or H. PLIENINGER et al., Chem. Ber., 94, 2088 (1961) when the acid is a cyclohexadienylcarboxylic acid.

The amines of general formula (III) in which the symbol Het bears an alkyloxy or alkylthio substituent, optionally substituted with an alkylamino radical or dialkylamino radical (in which the alkyl portions can form, with the nitrogen atom to which they are attached, a heterocyclic system as defined above according to the addition), or with an N-alkyl-N-(alkyloxycarbonyl)amino or dialkylcarbamoyl radical, can be prepared from the corresponding amine in which the symbol Het is a 1,8-naphthyridin-2-yl radical substituted at the 7-position with a halogen atom (preferably a chlorine atom), by the action, respectively, of a hydroxyl derivative or of a thiol of general formulae:

or

in which R' is an alkyl radical optionally bearing a substituent as defined above, in basic medium or by the action of the corresponding alcoholate or thiolate.

The reaction is generally performed in the presence of a strong base (e.g. sodium hydroxide, potassium hydroxide, quaternary ammonium hydroxide or sodium ethylate), at a temperature of between 50° and 150° C., or alternatively in the presence of the corresponding alcoholate or thiolate (e.g. sodium alcoholate), in a solvent such as an amide (e.g. dimethylformamide), an ether (e.g. tetrahydrofuran or dimethoxyethane), a chlorinated solvent (e.g. chlorobenzene), an aromatic hydrocarbon (e.g. toluene) or an oxide (e.g. dimethyl sulphoxide), or without a solvent, in the presence of an excess of hydroxyl derivative or thiol, at a temperature of between 70° C. and the refluxing temperature of the reaction mixture. Optionally, the reaction is performed in the presence of a phase transfer catalytic agent (e.g. tris(5,6-dioxaheptyl)amine or benzyltriethylammonium chloride).

When the alcoholate or the thiolate is used, the latter is obtained beforehand by the action of sodium on the alcohol of general formula (VIa) or the thiol of general formula (VIb), at a temperature of between 20° and 80° C., or by the action of sodium hydride at a temperature of between 0° and 20° C. in a solvent such as dimethylformamide, dimethoxyethane or tetrahydrofuran. It is not necessary to isolate the alcoholate obtained in order to use it in the following reaction.

The amine Het-NH$_2$ in which Het is a 1,8-naphthyridin-2-yl radical substituted in the 7-position with a halogen atom can be prepared in accordance with the method described by S. CARBONI, Gazz. Chim. Italiana, 96, 1456 (1966).

The amines of general formula (III) in which the symbol Het bears an alkylsulphinyl substituent which is itself substituted as defined above, can be prepared by oxidation of the corresponding amine of general formula (III) in which the symbol Het bears a substituted alkylthio radical.

The reaction is performed under conditions similar to those described above for the preparation of an amide of general formula (I) in which Het bears a substituted alkylsulphinyl substituent, starting with an amide of general formula (I) in which Het bears a substituted alkylthio radical.

As an option, it may be advantageous to protect the amine group prior to the reaction. In such a case, any suitable protective group is used, the introduction and removal of which do not adversely affect the remainder of the molecule and which is inert with respect to the oxidation reaction. For example, the protection may be accomplished in the form of chloroacetamido or phthalimido groups.

The products of general formula (IV) can be prepared according to the methods described by H. BREDERECK et al., Chem. Ber., 101, 41 (1968) and Angew. Chem. Internat. Ed., 2, 738 (1963).

The products of general formula (V) can be prepared by a method analogous to that for preparing the products according to the invention, by the action of an acid of general formula (II), or a reactive derivative of this acid, on 2-amino-7-methyl-1,8-naphthyridine.

2-Amino-7-methyl-1,8-naphthyridine can be obtained according to the method described by E. V. BROWN, J. Org. Chem., 30, 1607 (1965).

The new amides according to the present invention can be converted, where appropriate, into addition salts with acids.

As pharmaceutically acceptable salts, the addition salts with inorganic acids (e.g. hydrochlorides, hydrobromides, sulphates, nitrates or phosphates) or organic acids (e.g. succinates, fumarates, maleates or p-toluenesulphonates) may be mentioned.

The new amides according to the present invention can be purified, where appropriate, by physical methods such as crystallization or chromatography.

The products of general formula (I) according to the invention possess especially advantageous pharmacological properties. They show a high level of activity as anxiolytics, hypnotics, anticonvulsants, antiepileptic agents and muscle relaxants, which is demonstrated in the tests below.

In particular, they possess high affinity in vitro for benzodiazepine receptor sites at concentrations between 10 and about 1000 nM using the experimental technique described by J. C. BLANCHARD and L. JULOU, J. of Neurochemistry, 40, 601 (1983), modelled on the work of SQUIRES and BRAESTRUP, Nature, 266, 732 (1977).

In animals (mice) they were shown to be active at doses between 10 and 200 mg/kg orally, in controlling convulsions induced by pentetrazol using an experimental technique similar to that of EVERETT and RICHARDS, J. Pharmacol., 81, 402 (1944).

Furthermore, the amides of formula (I) have low toxicity: their oral LD$_{50}$ in mice is between 300 mg/kg and doses above 900 mg/kg.

Of special value are the amides of formula (I) in which—either (A) R denotes phenyl or phenyl substituted by 1 or 2 fluorine atoms or by alkyloxy, alkylamino or alkyloxycarbonylamino radical at the 4-position and Het denotes 1,8-naphthyridin-2-yl substituted at the 7-position by alkyloxy, alkylthio or alkylsulphinyl, said radicals being substituted by dialkylamino (in which the alkyls may be joined to form, with the nitrogen atom to which they are attached, a 6-membered heterocyclic system optionally containing another hetero atom chosen from nitrogen, oxygen and sulphur and optionally substituted by alkyl), by N-alkyl-N-(alkyloxycarbonyl)amino, or the said 1,8-naphthyridinyl radical is substituted at the 7-position by dialkylaminovinyl,- or (B) R denotes 4-alkylamino)phenyl or 4-(alkyloxycarbonylamino)phenyl and Het denotes 1,8-naphthyridin-2-yl substituted at the 7-position by alkyloxy, the said alkyl radicals or alkyl portions mentioned above being linear or branched and containing 1 to 4 carbon atoms each.

Among these products, those which are more especially active are the amides of formula (I) in which R denotes phenyl substituted by one or two fluorine atoms or by alkoxy at the 4-position and Het denotes 1,8-naphthyridin-2-yl substituted at the 7-position by alkyloxy or alkylthio containing 2 or 3 carbon atoms, said radicals being substituted by dialkylamino in which the alkyl portions contain 1 or 2 carbon atoms each; and in particular:

N-[7-(3-dimethylaminopropoxy)-1,8-naphthyridin-2-yl]-4-methoxybenzamide,

N-[7-(3-diethylaminopropoxy)-1,8-naphthyridin-2-yl]-4-methoxybenzamide,

N-[7-(2-dimethylaminoethylthio)-1,8-naphthyridin-2-yl]-4-methoxybenzamide,

N-[7-(3-dimethylaminopropylthio)-1,8-naphthyridin-2-yl]-4-methoxybenzamide, and

N-[7-(3-dimethylaminopropoxy)-1,8-naphthyridin-2-yl]-2,6-difluorobenzamide.

The examples which follow illustrate the present invention.

EXAMPLE 1

N,N'-Carbonyldiimidazole (10.9 g) is added to a solution of 4-methoxybenzoic acid (10.2 g) in anhydrous tetrahydrofuran (2000 cc). An immediate evolution of gas is observed. The mixture is stirred for 2 hours at a temperature in the region of 20° C. until the evolution of gas has ceased. 2-Amino-7-(2-dimethylaminoethoxy)-1,8-naphthyridine (11.6 g) is then added and the mixture is then heated under reflux for 25 hours. The mixture is poured into distilled water (1200 cc), and the precipitate formed in separated by filtration, washed with water and then dried in the air and finally under reduced pressure (0.07 kPa) at 30° C.

The solid obtained (5.3 g) is dissolved in boiling ethanol (50 cc). After 15 hours' cooling at 4° C., the crystallized product is separated by filtration, washed with ethanol (2×10 cc) and dried at 20° C. at reduced pressure (0.07 kPa). N-[7-(2-Dimethylaminoethoxy)-1,8-naphthyridin-2-yl]-4-methoxybenzamide (4.5 g), m.p. 77°-80° C., is obtained.

2-Amino-7-(2-dimethylaminoethoxy)-1,8-naphthyridine can be prepared in the following manner:

A mixture composed of 2-amino-7-chloro-1,8-naphthyridine (89.7 g), 2-dimethylaminoethanol (178 g) and potassium hydroxide pellets (85% pure; 65.8 g) is heated for 2 hours 30 minutes to 120° C. The mixture obtained is poured into distilled water (1500 cc). The precipitated product is removed by filtration.

The filtrate is extracted with methylene chloride (3×300 cc). The organic extracts are washed with distilled water (2×200 cc), dried over magnesium sulphate and concentrated to dryness at 60° C. under reduced pressure (4 kPa).

The product obtained is suspended in isopropyl ether (150 cc). After 1 hour's stirring at 25° C., the insoluble product is filtered off and then washed with isopropyl ether (25 cc) and dried at 20° C. under reduced pressure (0.07 kPa). 2-Amino-7-(2-dimethylaminoethoxy)-1,8-naphthyridine (45.8 g), m.p. 105° C., is thereby obtained.

EXAMPLE 2

The procedure is similar to that described in Example 1, but starting with 4-methoxybenzoic acid (10 g), N,N'-carbonyldiimidazole (10.7 g) and 2-amino-7-(3-dimethylaminopropoxy)-1,8-naphthyridine (10.9 g), heating for 6 hours under reflux. The reaction mixture is poured into water (300 cc) and extracted with methylene chloride (3×100 cc). After concentration of the organic phases to dryness under reduced pressure (4 kPa), the oily residue obtained (21.4 g) is treated with isopropyl ether (100 cc), with stirring. The crystallized solid obtained (13.9 g; m.p. approximately 80° C.) is purified by chromatography on a column 34 mm in diameter containing silica (140 g; 0.06-0.20 mm), eluting with a mixture (95:5 by volume) of methylene chloride and methanol and collecting 50-cc fractions. After concentration of fractions 41 to 99 to dryness at 40° C. under reduced pressure (4 kPa), a thick oil (10.1 g) is obtained which is stirred with isopropyl ether (110 cc). The solid obtained (4.3 g; m.p. approximately 80° C.) is again purified by flash chromatography under 30 kPa on a column 40 mm in diameter containing silica (130 g; 0.04-0.06 mm), eluting with a mixture (97:3 by volume) of methylene chloride and methanol and collecting 25-cc fractions. After concentration of fractions 10 to 50 to dryness at 40° C. under reduced pressure (4 kPa) and after drying at 40° C. under reduced pressure (0.07 kPa), N-[7-(3-dimethylaminopropoxy)-1,8-naphthyridin-2-yl]-4-methoxybenzamide (1 g), m.p. 130° C., is obtained.

2-Amino-7-(3-dimethylaminopropoxy)-1,8-naphthyridine can be prepared in the following manner:

A suspension of 2-amino-7-chloro-1,8-naphthyridine (89.75 g) in 3-dimethylamino-1-propanol (236 cc) is preheated to approximately 30° C. Potassium hydroxide pellets (85% pure; 65.8 g) are then introduced gradually. The reaction is exothermic, and the temperature rises to 80° C. at the end of the addition. The reaction mixture is then heated for a further 30 minutes to 90° C., allowed to cool to 60° C. and then poured into water (1500 cc) in the presence of methylene chloride (500 cc). The decanted organic extracts are washed with water (2×200 cc), dried over magnesium sulphate and concentrated to dryness at 40° C. under reduced pressure (4 kPa). The product obtained in the form of an oil is crystallized by stirring in hexane (300 cc). The crystallized solid is then separated by filtration, washed with hexane and dried at 20° C. at reduced pressure (0.07 kPa). 2-Amino-7-(3-dimethylaminopropoxy)-1,8-naphthyridine (109 g), m.p. 88° C., is obtained.

EXAMPLE 3

The procedure is similar to that described in Example 1, but starting with 4-methoxybenzoic acid (7.1 g), N,N'-carbonyldiimidazole (7.6 g) and 2-amino-7-(3-dimethylamino-2-methylpropoxy)-1,8-naphthyridine (7.8 g). The reaction mixture is poured into distilled water (500 cc) and extracted with methylene chloride (4×100 cc). The organic extracts are washed with distilled water (100 cc), dried over magnesium sulphate and concentrated to dryness at 40° C. under reduced pressure (4 kPa).

The isolated product is dissolved in ethanol (50 cc), and the solution thereby obtained is then treated with a 4N ethereal solution of hydrochloric acid (9.1 cc). The precipitate formed is separated by filtration, washed with ethanol (10 cc) and dried at 40° C. under reduced pressure (0.07 kPa).

The product obtained is dissolved in boiling ethanol (550 cc). After 3 hours' cooling at 4° C., the crystallized solid is separated by filtration, washed with ethanol (10 cc) and dried at 40° C. under reduced pressure (0.07 kPa). N-[7-(3-Dimethylamino-2-methylpropoxy)-1,8-naphthyridin-2-yl]-4-methoxybenzamide hydrochloride (4.65 g), m.p. 260° C., is obtained.

2-Amino-7-(3-dimethylamino-2-methylpropoxy)-1,8-naphthyridine can be prepared in the following manner:

A mixture composed of 2-amino-7-chloro-1,8-naphthyridine (21 g), 3-dimethylamino-2-methylpropanol (54.8 g) and potassium hydroxide pellets (85% pure; 15.4 g) is heated for 3 hours 30 minutes to 120° C. The reaction mixture is then poured into distilled water (500 cc) and extracted with methylene chloride (3×300 cc). The organic extracts are washed with distilled water (3×200 cc), dried over magnesium sulphate and concentrated to dryness at 40° C. under reduced pressure (4 kPa).

The product obtained is dissolved in ethanol (50 cc) and the solution obtained is then treated with a 4N ethereal solution of hydrochloric acid (82.5 cc). The precipitate formed is separated by filtration, washed with ethanol (2×50 cc) and dried in the air.

The isolated product is dissolved in distilled water (200 cc) and the solution obtained is then treated with 5% strength aqueous sodium carbonate solution (450 cc). The mixture is extracted with methylene chloride (4×200 cc). The extracts are washed with distilled water (6×300 cc), dried over magnesium sulphate and concentrated to dryness at 40° C. under reduced pressure (4 kPa).

The product obtained is dissolved in boiling isopropyl ether (500 cc). After 18 hours' cooling at 4° C., the crystallized solid is separated by filtration, washed with isopropyl ether (2×10 cc) and dried at 40° C. under reduced pressure (0.07 kPa). 2-Amino-7-(3-dimethylamino-2-methylpropoxy)-1,8-naphthyridine (8.5 g, m.p. 108° C.), is obtained.

EXAMPLE 4

The procedure is similar to that described in Example 1, but starting with 4-methoxybenzoic acid (4.1 g), N,N'-carbonyldiimidazole (4.3 g) and 2-amino-7-(3-diethylaminopropoxy)-1,8-naphthyridine (5 g). The reaction mixture is then poured into distilled water (500 cc) and extracted with methylene chloride (2×100 cc). The organic extracts are washed with distilled water (100 cc), dried over magnesium sulphate and concentrated to dryness at 40° C. under reduced pressure (4 kPa).

The product obtained is dissolved in ethanol (15 cc) and the solution thereby obtained is treated with a 4N ethereal solution of hydrochloric acid (3.9 cc). The white precipitate formed is separated by filtration, washed with ethanol (10 cc) and dried at 40° C. under reduced pressure (0.07 kPa), and is then dissolved in boiling ethanol (100 cc). After 3 hours' cooling at 4° C., the crystallized solid is separated by filtration, washed with ethanol (10 cc) and dried at 40° C. under reduced pressure (0.07 kPa). N-[7-(3-Diethylaminopropoxy)-1,8-naphthyridin-2-yl]-4-methoxybenzamide (2.5 g), melting at 200° C. and then at 240° C., is obtained.

2-Amino-7-(3-diethylaminopropoxy)-1,8-naphthyridine can be prepared in the following manner:

A mixture composed of 2-amino-7-chloro-1,8-naphthyridine (26.9 g), 3-diethylamino-1-propanol (78 g) and potassium hydroxide pellets (85% pure; 19.74 g) is heated for 3 hours to 120° C. The reaction mixture is then poured into distilled water (500 cc) and extracted with methylene chloride (500 cc, then 3×50 cc). The organic extracts are washed with distilled water (500 cc), dried over magnesium sulphate and concentrated to dryness at 40° C. under reduced pressure (4 kPa).

The product obtained is dissolved in ethanol (100 cc) and a 3.5N ethereal solution of hydrochloric acid (10 cc) is added to the solution thereby obtained. The precipitate formed is separated by filtration, washed with ethanol (2×50 cc) and dried at 40° C. under reduced pressure (0.07 kPa).

The product obtained is dissolved in boiling methanol (100 cc). After 3 hours' cooling at 4° C., the crystallized solid is separated by filtration, washed with methanol (10 cc) and dried at 40° C. under reduced pressure (0.07 kPa), and is then dissolved in distilled water (10 cc). 5% strength sodium carbonate solution (55 cc) is added to the solution thereby obtained. The mixture is extracted with methylene chloride (3×60 cc). The organic extracts are washed with water (5×100 cc), dried over magnesium sulphate and concentrated to dryness at 40° C. under reduced pressure (4 kPa). 2-Amino-7-(3-diethylaminopropoxy)-1,8-naphthyridine (5 g) is thereby obtained in the form of a brown oil which is used as it is in the next stage of the synthesis.

EXAMPLE 5

The procedure is similar to that described in Example 1, but starting with 4-methoxybenzoic acid (9.9 g), N,N'-carbonyldiimidazole (10.5 g) and 2-amino-7-[2-(4-methyl-1-piperazinyl)ethoxy]-1,8-naphthyridine (14.2 g). The reaction mixture is poured into water (600 cc) and extracted with methylene chloride (3×150 cc). After concentration of the organic phases to dryness under reduced pressure (4 kPa), the residue obtained is dissolved in ethanol (150 cc) and the solution obtained is then treated with a 3.1N ethereal solution of hydrochloric acid (30.3 cc). The precipitate formed is filtered, washed with ethanol (15 cc) and dried at 45° C. under reduced pressure (0.07 kPa), and is then dissolved in distilled water (150 cc).

The solution obtained is alkalinized to pH 10 with 4N sodium hydroxide, and the product which precipitates is extracted with methylene chloride (150 cc). After decantation, the aqueous phase is extracted again with methylene chloride (2×150 cc). The organic extracts are washed with water (2×100 cc), dried over magnesium sulphate and concentrated to dryness at 70° C. under reduced pressure (4 kPa).

The oil obtained is dissolved in ethanol (50 cc). Fumaric acid (3.5 g) dissolved in ethanol (50 cc) is added to the solution thereby obtained. After 2 hours at 4° C., the crystallized solid is separated by filtration, washed with ethanol (15 cc) and dried at 40° C. under reduced pressure (0.07 kPa). N-{7-[2-(4-Methyl-1-piperazinyl]ethoxy]-1,8-naphthyridin-2-yl}-4-methoxybenzamide fumarate (10.2 g), m.p. 175° C., is thereby obtained.

2-Amino-7-[2-(4-methyl-1-piperazinyl)ethoxy]-1,8-naphthyridine can be prepared in the following manner:

A mixture composed of 2-amino-7-chloro-1,8-naphthyridine (18 g), 1-(2-hydroxyethyl)-4-methylpiperazine (2.88 g) and powdered potassium hydroxide (80% pure; 7 g) is heated for 6 hours 30 minutes to 105° C. The reaction mixture is then poured into distilled water (800 cc) and extracted with methylene chloride (3×200 cc). The organic extracts are washed with water, dried over magnesium sulphate and concentrated to dryness at 70° C. under reduced pressure (4 kPa).

The oily residue obtained is purified by chromatography on a column 32 mm in diameter containing neutral alumina (250 g), eluting with methylene chloride and collecting 50-cc fractions. After concentration of fractions 3 to 45 to dryness at 60° C. under reduced pressure (4 kPa), 2-amino-7-[2-(4-methyl-1-piperazinyl)ethoxy]-1,8-naphthyridine (10 g) is obtained in the form of a thick gum.

1-(2-Hydroxyethyl)-4-methylpiperazine can be prepared according to the method described by V. ZOTTA et al., Farmacia, 10, 605 (1962).

EXAMPLE 6

The procedure is similar to that described in Example 1, but starting with 4-methoxybenzoic acid (8 g), N,N'-carbonyldiimidazole (8.5 g) and 2-amino-7-(2-morpholinoethoxy)-1,8-naphthyridine (9.6 g). The product obtained by precipitation in water (500 cc) is extracted with methylene chloride (500 cc, then 2×250 cc). After being washed with water (250 cc) and dried over magnesium sulphate, the organic extracts are concentrated to dryness at 50° C. under reduced pressure (4 kPa).

The oil obtained (17.3 g) is purified by flash chromatography under reduced pressure (30 kPa) on a column 40 mm in diameter containing silica (173 g; 0.04–0.06 mm), eluting with a mixture (98:2 by volume) of methylene chloride and methanol and collecting 50-cc fractions.

The product obtained (13.4 g), after concentration of fractions 48 to 95 to dryness at 40° C. under reduced pressure (4 kPa), is dissolved in ethanol (100 cc) and then treated with a 3.8N ethereal solution of hydrochloric acid (9 cc). The precipitate formed is filtered off, washed with ethanol (3×20 cc) and diethyl ether (3×20 cc) and dried at 50° C. under reduced pressure (0.07 kPa). The product obtained is dissolved in boiling 1-propanol (250 cc). After 2 hours' cooling at 4° C., the crystallized solid is separated by filtration, washed with 1-propanol (3×20 cc) and dried at 40° C. under reduced pressure (0.07 kPa). N-[7-(2-Morpholinoethoxy)-1,8-naphthvridin-2-yl]-4-methoxybenzamide hydrochloride (9 g), m.p. 242° C., is obtained.

2-Amino-7-(2-morpholinoethoxy)-1,8-naphthyridine can be prepared in the following manner:

Tris(3,6-dioxaheptyl)amine (1.47 g), pulverized potassium hydroxide (80% pure, 6.75 g) and morpholinoethanol (12 g) are added to a suspension of 2-amino-7-chloro-1,8-naphthyridine (16.2 g) in chlorobenzene (450 cc). The mixture is brought to 120° C. and maintained at this temperature for 3 hours. The suspension obtained after cooling is separated by filtration. The separated product is washed with chlorobenzene (3×50 cc) and water (3×50 cc). The solid obtained is redissolved in methylene chloride (400 cc). The insoluble material which remains is removed by filtration. The filtrate is dried over magnesium sulphate and concentrated to dryness at 40° C. under reduced pressure (4 kPa). The crude product obtained (23.5 g; m.p. 164° C.) is stirred in the presence of isopropyl ether (100 cc), filtered and dried at 30° C. under reduced pressure (0.07 kPa). 2-Amino-7-(2-morpholinoethoxy)-1,8-naphthyridine (13.9 g), m.p. 164° C., is obtained.

EXAMPLE 7

The procedure is similar to that described in Example 1, but starting with 4-methoxybenzoic acid (21.3 g), N,N'-carbonyldiimidazole (22.7 g) and 2-amino-7-[2-(N-methyl-N-tert-butoxycarbonylamino)ethoxy]-1,8-naphthyridine (30.6 g). The reaction mixture is poured into water (1000 cc) and extracted with methylene chloride (2×500 cc). The organic extracts are washed with water (500 cc), dried over magnesium sulphate and concentrated to dryness at 50° C. under reduced pressure (4 kPa).

The oil obtained is purified by chromatography on a column 60 mm in diameter containing silica (400 g; 0.06–0.20 mm), eluting with a mixture (50:50 by volume) of ethyl acetate and cyclohexane and collecting 100-cc fractions. After concentration of fractions 6 to 20 to dryness at 40° C. under reduced pressure (4 kPa), a thick oil (35 g) is obtained. This product is dissolved in ethanol (75 cc), and a 3.8N ethereal solution of hydrochloric acid (4.35 cc) is then added. The precipitate formed is separated by filtration, washed with ethanol (3×20 cc) and dried at 40° C. under reduced pressure (0.07 kPa), and is then dissolved in boiling acetonitrile (280 cc). After 3 hours' cooling at 4° C., the crystallized product is filtered off, washed with acetonitrile (3×20 cc) and diethyl ether (3×20 cc) and dried at 50° C. under reduced pressure. N-{7-[2-(N-Methyl-N-tert-butxoycarbonylamino)ethoxy]-1,8-naphthyridin-2-yl}-4-methoxy benzamide hydrochloride (6.5 g), m.p. 194° C., is obtained.

2-Amino-7-[2-(N-methyl-N-tert-butoxycarbonylamino)ethoxy]-1,8-naphthyridine can be prepared in the following manner:

A mixture consisting of 2-amino-7-chloro-1,8-naphthyridine (112 g), toluene (1500 cc), 2-(N-methyl-N-tert-butoxycarbonylamino)ethanol (109.4 g), 50% strength (by weight) aqueous sodium hydroxide solution (350 g) and benzyltriethylammonium chloride (14.2 g) is stirred for 20 hours at a temperature of 50° C. The insoluble product is separated by filtration and washed with toluene (3×100 cc) and water (4×100 cc).

The organic phase of the filtrate is separated by decantation, washed with distilled water (3×300 cc), dried over magnesium sulphate and concentrated to dryness at 60° C. under reduced pressure (4 kPa). The residue obtained is dissolved in boiling acetonitrile (225 cc). After 2 hours' cooling at 4° C., the crystallized solid is separated by filtration, washed with acetonitrile (3×20 cc) and dried in the air. 2-Amino-7-[2-(N-methyl-N-tert-butoxycarbonylamino)ethoxy]-1,8-naphthyridine (30.6 g), m.p. 170° C., is obtained.

2-(N-Methyl-N-tert-butoxycarbonylamino)ethanol can be prepared in the following manner:

Sodium carbonate (70 g) is added gradually to a solution of 2-methylaminoethanol (50 g) in water (850 cc). The temperature rises gradually from 25° to 38° C. In the course of 5 minutes, a solution of di-tert-butyl dicarbonate (155 g) in dioxane (700 cc) is then poured in; the reaction is slightly exothermic. After 15 hours' stirring at approximately 20° C., the suspension obtained is separated by filtration and washed with water (100 cc). The filtrate is extracted with methylene chloride (3×500 cc), and the combined organic extracts are washed with water (500 cc), dried over magnesium sulphate and concentrated to dryness at 60° C. under reduced pressure (4 kPa). 2-(N-Methyl-N-tert-butoxycarbonylamino)ethanol (114.7 g) is obtained in the form of an oil.

Infrared spectrum, characteristic bands (cm$^{-1}$): 3625; 3430; 1675; 1395; 1368; 1160; 1050.

EXAMPLE 8

A solution of N-{7-[2-(N-Methyl-N-tert-butoxycarbonylamino)ethoxy]-1,8-naphthyridin-2-yl}-4-methoxybenzamide (20 g) in trifluoroacetic acid (60 cc) is stirred for 1 hour at a temperature in the region of 20° C. The reaction mixture is poured into water (100 cc) and neutralized with 4N sodium hydroxide (180 cc). The insoluble product obtained is separated by filtration, washed with water and dried in the air, and is then dissolved in boiling acetonitrile (250 cc). After 2 hours' cooling at 4° C., the crystallized solid is separated by filtration, washed with acetonitrile (3×20 cc) and dried at 50° C. under reduced pressure (0.07 kPa). N-[7-(2-Methylaminoethoxy)-1,8-naphthyridin-2-yl]-4-methoxybenzamide (8.7 g), m.p. 146° C., is obtained.

EXAMPLE 9

The procedure is similar to that described in Example 1, but starting with 4-methoxybenzoic acid, (9.3 g), N,N'-carbonyldiimidazole (9.9 g) and 2-amino-7-(dimethylcarbamoylmethoxy)-1,8-naphthyridine (10.1 g). The reaction mixture is poured into water (1250 cc) and the precipitate obtained is separated by filtration, washed with water and dried at 40° C. under reduced pressure (0.07 kPa). A solid (9.2 g) is obtained, m.p. approximately 110° C. The filtrate is extracted with methylene chloride (2×500 cc), washed with water and concentrated to dryness at 50° C. under reduced pressure (4 kPa) to give a gum (4 g). The two products thereby obtained are combined and purified by flash chromatography under reduced pressure (30 kPa) on a column 40 mm in diameter containing silica (160 g; 0.04–0.06 mm), eluting with a mixture (99:1 by volume) of methylene chloride and methanol and collecting 50-cc fractions. After concentration of fractions 23 to 120 to dryness at 40° C. under reduced pressure (4 kPa), an amorphous solid (7.3 g) is obtained. This product is stirred with ethyl ether (150 cc) and the crystallized solid obtained is filtered off, washed with ethyl ether and dried in the air. The crystallized solid is then dissolved in a boiling mixture (50 cc) of ethanol and water (50:50 by volume). After 2 hours' cooling at 4° C., the crystallized solid is separated by filtration, washed with the crystallization solvent (3×20 cc) and dried at 50° C. under reduced pressure (0.07 kPa). N-[7-(Dimethylcarbamoylmethoxy)-1,8-naphthyridin-2-yl]-4-methoxybenzamide (4.3 g), m.p. 165° C., is obtained.

2-Amino-7-(dimethylcarbamoylmethoxy)-1,8-naphthyridine can be prepared in the following manner:

Powdered potassium hydroxide (80% pure; 7.5 g) is added gradually to a suspension consisting of 2-amino-7-chloro-1,8-naphthyridine (12 g) and N,N-dimethylglycolamide (25.7 g), preheated to 70° C. The reaction is exothermic. The temperature is maintained in the region of 100° C. during the addition. When the addition is complete, the mixture is heated for a further 1 hour 30 minutes at 90° C. After being cooled, the reaction mixture is poured into water (200 cc). The mixture is extracted with methylene chloride (4×200 cc). The organic extracts are washed with water (200 cc), dried over magnesium sulphate and concentrated to dryness at 50° C. under reduced pressure (4 kPa).

The product obtained is stirred with ethyl ether (100 cc). The solid which crystallizes is filtered, washed with ethyl ether and dried at 50° C. under reduced pressure (0.07 kPa). 2-Amino-7-(dimethylcarbamoylmethoxy)-1,8-naphthyridine (10.2 g), m.p. 182° C., is thereby obtained.

N,N-Dimethylglycolamide can be prepared according to the method described by W. P. RATCHFORD et al., J. Org. Chem., 15, 317 (1950).

EXAMPLE 10

The procedure is similar to that described in Example 1, but starting with 4-methoxybenzoic acid (21.1 g), N,N'-carbonyldiimidazole (22.5 g) and 2-amino-7-(2-dimethylaminoethylthio)-1,8-naphthyridine (22 g). The product obtained after treating the reaction mixture under the conditions described in Example 1 and drying is dissolved in dimethylformamide (600 cc) and treated with a 3N ethereal solution of hydrochloric acid (52 cc). The precipitate formed is separated by filtration, washed with ethyl ether (3×30 cc) and dried at 40° C. under reduced pressure (0.07 kPa).

The product obtained is dissolved in boiling methanol (750 cc). After 3 hours' cooling at 4° C., the crystallized solid is separated by filtration, washed with methanol (30 cc) and dried at 40° C. under reduced pressure. N-[7-(2-Dimethylaminoethylthio)-1,8-naphthyridin-2-yl]-4-methoxybenzamide dihydrochloride (23.6 g), m.p. 260° C. with decomposition, is obtained.

2-Amino-7-(2-dimethylaminoethylthio)-1,8-naphthyridine can be prepared in the following manner:

A mixture composed of 2-amino-7-chloro-1,8-naphthyridine (29.6 g), 2-dimethylaminoethanethiol hydrochloride (48 g), potassium hydroxide pellets (85% pure; 43.5 g) and dimethyl sulphoxide (300 cc) is heated for 2 hours at 90° C. The reaction mixture is then poured into distilled water (400 cc) and extracted with methylene chloride (6×250 cc). The extracts are washed with distilled water (300 cc), dried over magnesium sulphate and concentrated to dryness at 40° C. under reduced pressure. The residue obtained is taken up with ethanol (100 cc) and the insoluble product is separated by filtration, washed with ethanol (2×30 cc) and dried at 40° C. under reduced pressure (0.07 kPa). 2-Amino-7-(2-dimethylaminoethylthio)-1,8-naphthyridine (22 g), m.p. 174° C., is obtained.

EXAMPLE 11

The procedure is similar to that described in Example 1, but starting with 4-methoxybenzoic acid (5.32 g), N,N'-carbonyldiimidazole (5.67 g) and 2-amino-7-(3-dimethylaminopropylthio)-1,8-naphthyridine (9 g). The reaction mixture is poured into distilled water (1000 cc) and extracted with methylene chloride (3×300 cc). The organic extracts are washed with distilled water (200 cc), dried over magnesium sulphate and concentrated to dryness at 40° C. under reduced pressure (4 kPa).

The red-brown paste obtained (9.32 g) is dissolved in ethanol (50 cc) and then treated with a 4.7N ethereal solution of hydrochloric acid (4.6 cc). The precipitate formed is separated by filtration, washed with ethyl ether (10 cc) and dried at 40° C. under reduced pressure (0.07 kPa), and is then dissolved in boiling 1-propanol (200 cc). After 15 hours' cooling at 4° C., the crystallized solid is separated by filtration, washed with 1-propanol (2×10 cc) and dried at 40° C. under reduced pressure (0.07 kPa). N-[7-(3-Dimethylaminopropylthio)-1,8-naphthyridin-2-yl]-4-methoxybenzamide hydrochloride (7.24 g), m.p. 210° C., is obtained.

2-Amino-7-(3-dimethylaminopropylthio)-1,8-naphthyridine can be prepared in the following manner:

A mixture composed of 2-amino-7-chloro-1,8-naphthyridine (8 g), 3-dimethylaminopropanethiol (11.4 g), potassium hydroxide pellets (85% pure; 6.26 g) and dimethyl sulphoxide (87 cc) is heated to 90° C. for 3 hours 30 minutes. The reaction mixture is then poured into water (1500 cc) and extracted with methylene chloride (5×400 cc). The organic extracts are combined and washed with distilled water (400 cc), dried over magnesium sulphate and concentrated to dryness at 40° C. under reduced pressure (4 kPa). The residue obtained is treated with ethyl ether (100 cc). The insoluble product is separated by filtration, washed with ethyl ether (10 cc) and dried at 40° C. under reduced pressure (0.07 kPa). 2-Amino-7-(3-dimethylaminopropylthio)-1,8-naphthyridine (9 g), m.p. 164° C., is obtained.

EXAMPLE 12

The procedure is similar to that described in Example 1, but starting with benzoic acid (5.5 g), N,N'-carbonyldiimidazole (8.1 g) and 2-amino-7-(2-dimethylaminoethoxy)-1,8-naphthyridine (11.6 g), heating for 5 hours under reflux. The reaction mixture is poured into water (1500 cc) and extracted with ethyl acetate (2×1000 cc). After concentration of the organic phases to dryness under reduced pressure (4 kPa), the oily residue obtained (9.2 g) is dissolved in boiling ethyl acetate (25 cc). Then, after 2 hours' cooling at 4° C., the crystallized solid is separated by filtration, washed with ethyl acetate (3 cc) and dried at 40° C. under reduced pressure (0.07 kPa). N-[7-(2-Dimethylaminoethoxy)-1,8-naphthyridin-2-yl]benzamide (4.5 g), m.p. 109° C., is obtained.

EXAMPLE 13

The procedure is similar to that described in Example 1, but starting with 2,6-difluorobenzoic acid (11.3 g), N,N'-carbonyldiimidazole (12.9 g) and 2-amino-7-(3-dimethylaminopropoxy)-1,8-naphthyridine (11.8 g). The product obtained by precipitation in water followed by drying is dissolved in boiling acetone (450 cc). After 3 hours' cooling at 4° C., the crystallized solid is separated by filtration, washed with acetone (10 cc) and dried at 40° C. under reduced pressure (0.07 kPa). N-[7-(3-Dimethylaminopropoxy)-1,8-naphthyridin-2-yl]-2,6-difluorobenzamide (7.2 g), m.p. 190° C., is obtained.

EXAMPLE 14

The procedure is similar to that described in Example 1, but starting with 4-(N-ethyltrifluoroacetamido)benzoic acid (7 g), N,N'-carbonyldiimidazole (4.2 g) and 2-amino-7-methoxy-1,8-naphthyridine (3.5 g). The reaction mixture is then poured into water (1000 cc) and extracted with methylene chloride (2×200 cc). The organic extracts are dried over magnesium sulphate and concentrated to dryness at 40° C. under reduced pressure (4 kPa).

The product obtained is dissolved in methanol (20 cc) under reflux, and then treated with isopropyl ether (150 cc). The precipitate formed is separated by filtration, washed with isopropyl ether (2×10 cc) and dried at 40° C. under reduced pressure (0.07 kPa). N-(7-Methoxy-1,8-naphthyridin-2-yl)-4-(N'-ethyltrifluoroacetamido)-benzamide (5.1 g), m.p. 150° C., is obtained.

A mixture composed of N-(7-methoxy-1,8-naphthyridin-2-yl)-4-(N'-ethyltrifluoroacetamido)benzamide (5 g), 7% strength aqueous potassium carbonate solution (125 cc) and methanol (25 cc) is heated to 80° C. for 15 minutes. The precipitate formed is separated by filtration, washed with distilled water (4×20 cc) and dried at 40° C. under reduced pressure (0.07 kPa).

This product is dissolved in boiling methanol (50 cc). After 2 hours' cooling at 20° C., the crystallized solid is separated by filtration, washed with methanol (10 cc) and dried at 40° C. under reduced pressure. N-(7-Methoxy-1,8-naphthyridin-2-yl)-4-ethylaminobenzamide (2.2 g), melting at 134° C. and then at 174° C., is obtained.

4-(N-Ethyltrifluoroacetamido)benzoic acid can be prepared in the following manner:

A mixture composed of 4-ethylaminobenzoic acid (18 g), trifluoroacetic anhydride (20.7 cc) and tetrahydrofuran (100 cc) is left stirring for 5 hours at 25° C. The mixture is then poured into water (200 cc) and extracted with methylene chloride (2×200 cc). The organic extracts are washed with distilled water (220 cc), dried over magnesium sulphate and concentrated to dryness at 40° C. under reduced pressure (4 kPa). The product obtained is purified by chromatography on a column 40 mm in diameter containing silica (320 g; 0.04–0.06 mm), eluting with a mixture (98:2 by volume) of methylene chloride and methanol and collecting 20-cc fractions. After concentration of fractions 2 to 21 to dryness at 40° C. under reduced pressure (4 kPa), 4-(N-ethyltrifluoroacetamido)benzoic acid (7 g), m.p. 132° C., is obtained.

4-Ethylaminobenzoic acid can be prepared in the following manner:

A mixture composed of 4-aminobenzoic acid (30 g), sodium borohydride (32.3 g) and acetic acid (550 cc) is left stirring for 26 hours at 25° C. The reaction mixture is then concentrated to dryness at 70° C. under reduced pressure (4 kPa). The product obtained is treated with distilled water (2000 cc) and the precipitate formed is separated by filtration, washed with distilled water (20 cc) and dried in the air. The product obtained is dissolved in boiling acetonitrile (250 cc). After 2 hours' cooling at 25° C., the crystallized solid is separated by filtration, washed with acetonitrile (10 cc) and dried at 40° C. under reduced pressure (0.07 kPa). 4-Ethylaminobenzoic acid (18 g), m.p. 174° C., is obtained.

EXAMPLE 15

The procedure is similar to that described in Example 1, but starting with 4-(ethoxycarbonylamino)benzoic acid (7.3 g), N,N'-carbonyldiimidazole (5.6 g) and 2-amino-7-methoxy-1,8-naphthyridine (4.7 g). The reaction mixture is then poured into water and the white precipitate formed is separated by filtration, washed with water (10 cc) and dried in the air for 18 hours.

The product obtained (9.5 g; m.p. 194° C.) is dissolved in boiling acetonitrile (150 cc). After 2 hours' cooling at 25° C., the crystallized solid is separated by filtration, washed with acetonitrile (2×10 cc) and dried at 40° C. under reduced pressure. N-(7-Methoxy-1,8-naphthyridin-2-yl)-4-(ethoxycarbonylamino)benzamide (6.5 g), m.p. 200° C., is obtained.

4-(Ethoxycarbonylamino)benzoic acid can be prepared in the following manner:

A mixture composed of 4-aminobenzoic acid (10 g), 1N aqueous sodium bicarbonate solution (365 cc) and ethyl chloroformate (7 cc) is left stirring for 30 minutes at 5° C. 2.5N hydrochloric acid (150 cc) is then added to the reaction mixture. The precipitate formed is separated by filtration, washed with water (3×200 cc) and dried at 40° C. under reduced pressure (0.07 kPa). 4-(Ethoxycarbonylamino)benzoic acid (13.8 g), m.p. 207° C., is obtained.

EXAMPLE 16

The procedure is similar to that described in Example 1, but starting with cyclopropanecarboxylic acid (5.75 g), N,N'-carbonyldiimidazole (10.9 g) and 2-amino-7-(3-dimethylaminopropoxy)-1,8-naphthyridine (12.3 g). The reaction mixture is poured into water (800 cc) and extracted with methylene chloride (3×200 cc). The combined organic extracts are washed with water (3×100 cc), dried over magnesium sulphate and concentrated to dryness under reduced pressure (4 kPa). The oil obtained is dissolved in ethanol (50 cc) at 40° C.; after treatment with charcoal, distilled water (150 cc) is added to the filtrate. After 4 hours' cooling at 4° C., the solid obtained is separated by filtration, washed with a mixture (20 cc) of ethanol and water (1:3 by volume) and dried at 20° C. under reduced pressure (0.07 kPa).

The solid obtained (12 g) is dissolved in ethanol (20 cc). Fumaric acid (4.4 g) dissolved in ethanol (50 cc) is added to the solution thereby obtained. After 2 hours at 4° C., the crystallized solid is separated by filtration, washed with ethanol (20 cc) and dried at 40° C. under reduced pressure (0.07 kPa). N-[7-(3-dimethylaminopropoxy)-1,8-naphthyridin-2-yl]cyclopropanecarboxamide fumarate (11 g), m.p. 210° C., is thereby obtained.

EXAMPLE 17

3-Chloroperbenzoic acid (3.6 g) is added to a solution of N-[7-(2-dimethylaminoethylthio)-1,8-naphthyridin-2-yl]-4-methoxybenzamide (6 g) in methylene chloride (90 cc) at 0° C. After 2 hours' stirring at 0° C., the reaction mixture is poured into 5% strength sodium carbonate solution (200 cc) and extracted with methylene chloride (4×100 cc). The organic extracts are washed with distilled water (100 cc), dried over magnesium sulphate and concentrated at 40° C. under reduced pressure (4 kPa).

The product is separated by flash chromatography under reduced pressure (30 kPa) on silica (50 g;

0.04–0.06 mm), eluting with a mixture (95:5 by volume) of methylene chloride and methanol and collecting 50-cc fractions. After concentration of fractions 3 to 13 to dryness at 40° C. under reduced pressure (4 kPa), a solid (2.3 g) is obtained, m.p. 140° C. This product is dissolved in boiling acetonitrile (30 cc). After 1 hour's cooling at 5° C., the crystallized solid is separated by filtration, washed with ethyl ether (2×10 cc) and dried at 40° C. under reduced pressure (0.07 kPa). N-[7-(2-Dimethylaminoethylsulphinyl)-1,8-naphthyridin-2-yl]-4-methoxybenzamide (2.2 g), m.p. 158° C., is obtained.

EXAMPLE 18

Tert-butoxybis(dimethylamino)methane (28 g) is added to a suspension composed of N-(7-methyl-1,8-naphthyridin-2-yl)-4-methoxybenzamide (12 g) and anhydrous dimethylformamide (12 cc). The mixture is stirred for 3 hours at 130° C. The solution obtained is poured into water (100 cc) and the mixture extracted with methylene chloride (200 cc). The organic extracts are washed with water (2×100 cc), dried over magnesium sulphate and concentrated to dryness at 50° C. under reduced pressure (0.5 kPa). The amorphous residue obtained is dissolved in boiling carbon tetrachloride (100 cc). A solid is precipitated by slowly adding isopropyl ether (150 cc). The crystallized solid obtained is separated by filtration, washed with isopropyl ether (30 cc) and dried in the air. The base obtained (9.2 g; m.p. approximately 110° C.) is dissolved in ethanol (150 cc) and a 4.7N solution (20 cc) of hydrochloric acid in ethyl ether is added. The precipitate obtained is separated by filtration, washed with ethyl ether (3×30 cc) and dried at 25° C. under reduced pressure (4 kPa). The crude hydrochloride obtained is purified by recrystallization in ethanol (160 cc). N-[7-(2-Dimethylaminovinyl)-1,8-naphthyridin-2-yl]-4-methoxybenzamide in the hydrochloride state (6 g), m.p. 240° C., is thereby obtained.

The preparation of N-(7-methyl-1,8-naphthyridin-2-yl)-4-methoxybenzamide has been described previously in French Patent Application No. 2,567,887.

The present invention also provides the pharmaceutical compositions comprising an amide of formula (I) in the pure state or in combination with a compatible and pharmaceutically acceptable adjuvant, diluent and/or coating. These pharmaceutical compositions can be employed orally, rectally, parenterally or percutaneously.

As solid compositions for oral administration, tablets, pills, powders (generally in gelatin capsules) or granules may be used. In these compositions, the active product according to the invention is mixed with one or more inert diluents such as sucrose, lactose or starch. These compositions can also include substances other than the diluents, e.g. a lubricant such as magnesium stearate.

As liquid compositions for oral administration, emulsions which are pharmaceutically acceptable, solutions, suspensions, syrups and elixirs containing inert diluents such as water or liquid paraffin may be used. These compositions can also include substances other than the diluents, e.g. wetting agents, sweeteners or flavourings.

The compositions according to the invention for parenteral administration can be aqueous or non-aqueous sterile solutions, suspensions or emulsions. As a solvent or vehicle, propylene glycol, a polyethylene glycol, vegetable oils, especially olive oil, or injectable organic esters, e.g. ethyl oleate, may be employed. These compositions can also contain adjuvants, especially wetting agents, emulsifiers and dispersants. The sterilization can be carried out in several ways, e.g. by means of a bacteriological filter, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories which can contain, in addition to the active product, excipients such as cocoa butter or suppo-wax.

The compositions for percutaneous administration are creams, ointments, lotions and liniments, in which the active product is combined with liquid or pasty excipients, preferably in combination with a vehicle which promotes percutaneous migration.

The compositions according to the invention are especially useful in human therapy on account of their anxiolytic, hypnotic, anticonvulsant, anti-epileptic and muscle relaxant action.

In human therapy, the dose used depends on the effect sought and the length of the treatment; the dose is generally between 10 and 500 mg per day orally for an adult.

In general, the doctor will determine the dosage which he judges to be most suitable in relation to the age, weight and all other factors specific to the subject to be treated.

The Examples which follow illustrate compositions according to the invention.

EXAMPLE A

Tablets containing 10-mg doses of active product and having the following composition are prepared by the customary technique:

| | |
|---|---|
| N—[7-(3-Dimethylaminopropoxy)-1,8-naphthyridin-2-yl]-4-methoxybenzamide | 0.010 g |
| starch | 0.200 g |
| precipitated silica | 0.036 g |
| magnesium stearate | 0.004 g |

EXAMPLE B

Tablets containing 10-mg doses of active product and having the following composition are prepared according to the customary technique:

| | |
|---|---|
| N—[7-(2-dimethylaminoethylthio)-1,8-naphthyridin-2-yl]-4-methoxybenzamide dihydrochloride | 0.012 g |
| starch | 0.200 g |
| precipitated silica | 0.036 g |
| magnesium stearate | 0.004 g |

We claim:

1. A substituted amide of the formula:

R—CONH—Het and its pharmaceutically acceptable acid addition salts, in which either
(A) R denotes
cycloalkyl of 3 to 6 carbon atoms,
cyclohexadienyl,
phenyl, or
phenyl substituted by
1 to 2 fluorine atoms, by
hydroxyl, by alkyl or alkyloxy at the 3- or 4-position, by methylenedioxy at the 3- and 4-positions by dialkylamino at the 2- or 3-position or by alkylamino or alkyloxycarbonylamino at the 4-position, or R denotes 3-pyridyl,
alkyloxy-3-pyridyl,
thienyl,
alkylthienyl,
furyl,
tetrahydropyridyl,
pyridazinyl or
alkylpyridazinyl, and Het denotes
1,8-naphthyridin-2-yl substituted at the 7-position by
alkyloxy
alkylthio or
alkylsulphinyl said radicals being substituted by alkylamino, by dialkylamino in which the alkyls may be joined to form,
with the nitrogen atom to which they are attached, a 5- or 6-membered heterocyclic system optionally containing another hetero atom chosen from nitrogen, oxygen and sulphur and optionally substituted by alkyl, by N-alkyl-N-(alkyloxycarbonyl)amino or by dialkylcarbamoyl, or the said 1,8-naphthyridinyl radical is substituted at the 7-position by dialkylaminovinyl; or (B) R denotes
4-(alkylamino)phenyl or
4-(alkyloxycarbonylamino)phenyl, and Het denotes
1,8-naphthyridin-2-yl substituted at the 7-position by alkyloxy or alkylthio;
the aforesaid alkyl radicals and alkyl portions mentioned above being linear or branched and containing 1 to 4 carbon atoms each.

2. An amide according to claim 1, and its pharmaceutically acceptable acid addition salts, in which—either (A) R denotes phenyl or phenyl substituted by 1 or 2 fluorine atoms or by alkyloxy, alkylamino or alkyloxycarbonylamino at the 4-position, and Het denotes 1,8-naphthyridin-2-yl substituted at the 7-position by alkyloxy, alkylthio or alkylsulphinyl said radicals being substituted by dialkylamino (in which the alkyls may be joined to form, with the nitrogen atom to which they are attached, a 6-membered heterocyclic system optionally containing another hetero atom chosen from nitrogen, oxygen and sulphur and optionally substituted by alkyl), by N-alkyl-N-(alkyloxycarbonyl) amino, or the said 1,8-naphthyridinyl radical is substituted at the 7-position by dialkylaminovinyl;

or (B) R denotes 4-(alkylamino)phenyl or 4-(alkyloxycarbonylamino)phenyl and Het denotes 1,8-naphthyridin-2-yl substituted at the 7-position by alkyloxy, the aforesaid alkyl radicals and alkyl portions mentioned above being linear or branched and containing 1 to 4 carbon atoms each.

3. An amide according to claim 1, and its pharmaceutically acceptable acid addition salts, in which R denotes phenyl substituted by one or two fluorine atoms or by alkyloxy at the 4-position and Het denotes 1,8-naphthyridin-2-yl substituted at the 7-position by alkyloxy or alkylthio containing 2 or 3 carbon atoms, said radicals being substituted by dialkylamino in which the alkyl portions contain 1 or 2 carbon atoms each.

4. An amide according to claim 1 which is N-[7-(3-Dimethylaminopropoxy)-1,8-naphthyridin-2-yl]-4-methoxybenzamide, and its pharmaceutically acceptable acid addition salts.

5. An amide according to claim 1 which is N-[7-(3-Diethylaminopropoxy)-1,8-naphthyridin-2-yl]-4-methoxybenzamide, and its pharmaceutically acceptable acid addition salts.

6. An amide according to claim 1 which is N-[7-(2-Dimethylaminoethylthio)-1,8-naphthyridin-2-yl]-4-methoxybenzamide, and its pharmaceutically acceptable acid addition salts.

7. An amide according to claim 1 which is N-[7-(3-Dimethylaminopropylthio)-1,8-naphthyridin-2-yl]-4-methoxybenzamide, and its pharmaceutically acceptable acid addition salts.

8. An amide according to claim 1 which is N-[7-(3-Dimethylaminopropoxy)-1,8-naphthyridin-2-yl]-2,6-difluorobenzamide, and its pharmaceutically acceptable acid addition salts.

9. Method of producing an anxiolytic, hypnotic, anticonvulsant, anti-epileptic, or muscle relaxant effect in a subject in whom such an effect is desired which comprises administering to such subject an effective amount for the effect sought of an amide as defined in claim 1.

10. A pharmaceutical composition useful as an anxiolytic, hypnotic, anticonvulsant, antiepileptic, or muscle relaxant which contains an effective amount of at least one amide according to claim 1 as such or as a pharmaceutically acceptable acid addition salt, in combination with one or more diluents or adjuvants which are compatible and pharmaceutically acceptable.

* * * * *